Figure 2:
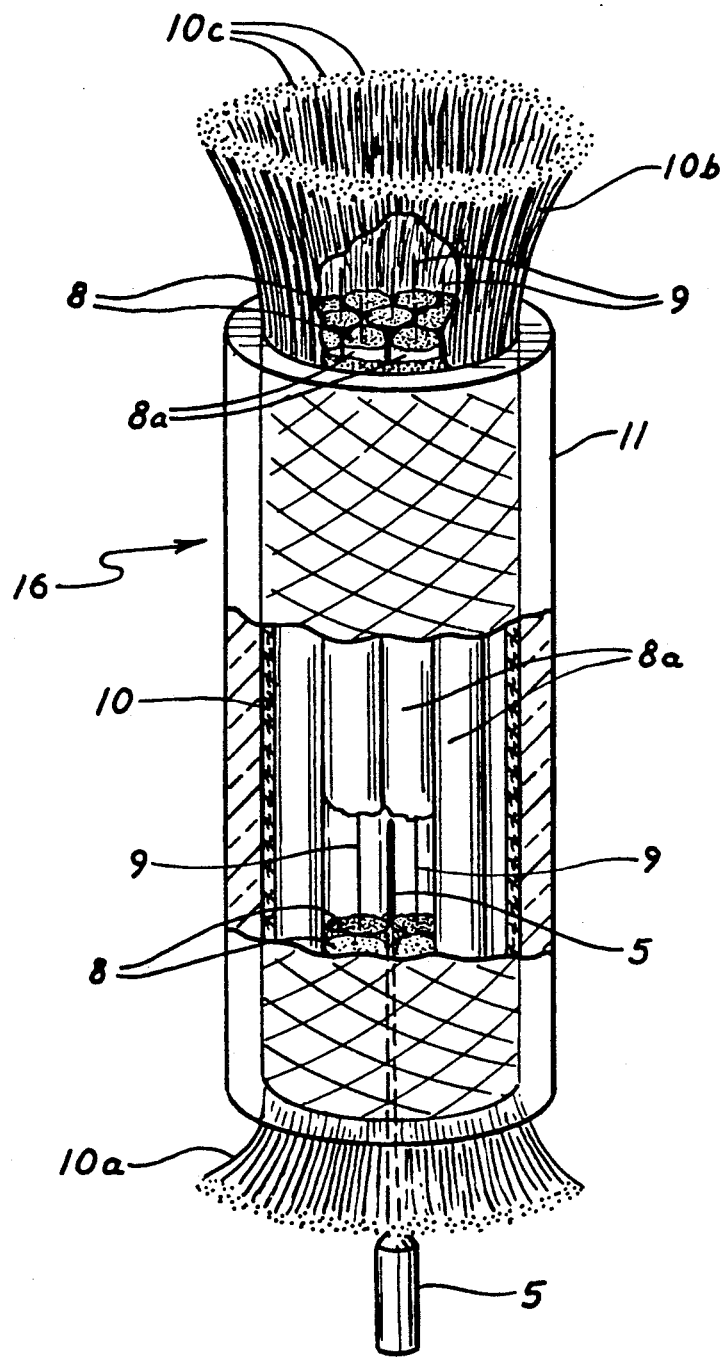

United States Patent [19]

Peltier

[11] Patent Number: 5,196,171
[45] Date of Patent: Mar. 23, 1993

[54] ELECTROSTATIC VAPOR/AEROSOL/AIR ION GENERATOR

[75] Inventor: Mark E. Peltier, So. St. Paul, Minn.

[73] Assignee: In-Vironmental Integrity, Inc., Minneapolis, Minn.

[21] Appl. No.: 667,200

[22] Filed: Mar. 11, 1991

[51] Int. Cl.⁵ .............................................. A61L 9/12
[52] U.S. Cl. .......................................... 422/121; 422/4; 422/5; 422/122; 422/123; 422/125; 422/305; 239/34; 239/44; 239/706
[58] Field of Search ................. 422/4, 5, 22, 121, 122, 422/123, 125, 305; 239/34, 44, 706; 261/94, 100; 392/336, 338

[56] References Cited

U.S. PATENT DOCUMENTS

| | | | |
|---|---|---|---|
| 2,140,516 | 12/1938 | Cowan | 392/338 |
| 2,692,327 | 10/1954 | Avrigan, Jr. | 422/305 |
| 2,931,880 | 4/1960 | Yaffe | 422/125 |
| 3,431,393 | 3/1969 | Katsuda | 422/305 |
| 3,518,409 | 6/1970 | Corbett | 422/305 |
| 3,610,879 | 10/1971 | Katzman et al. | 422/305 |
| 3,659,078 | 4/1972 | Rudstrom | 422/305 |
| 3,714,392 | 1/1973 | Katzman et al. | 422/305 |
| 3,771,233 | 11/1973 | French et al. | 159/DIG. 26 |
| 4,400,332 | 8/1983 | Pollard et al. | 239/706 |
| 4,419,302 | 12/1983 | Nishino et al. | 422/125 |
| 4,776,515 | 10/1988 | Michalchik | 239/3 |
| 4,829,996 | 5/1989 | Noakes et al. | 239/706 |

Primary Examiner—Robert J. Warden
Assistant Examiner—Timothy M. McMahon
Attorney, Agent, or Firm—Moore & Hansen

[57] ABSTRACT

The controlled generation of vapors and/or aerosols from liquids is accomplished by applying a regulated, DC voltage to a wick-like, porous emitter or generator assembly which is supplied with the desired liquid to be vaporized. An electrostatic charge is applied to the liquid by means of an electrode positioned in contact with the wick assembly and connected to the DC power supply. The wick assembly includes a porous, capillary material, such as braided fibers, through which the liquid passes to exposed, vapor-emitting fiber tips.

The environment in a room, or enclosed space of any kind, may be aromatically conditioned and/or have its quality modified and enhanced by using a selected liquid conditioning substance such as an aromatic oil, deodorant, disinfectant, fumigant, fungicide, insecticide, or bactericide.

16 Claims, 6 Drawing Sheets

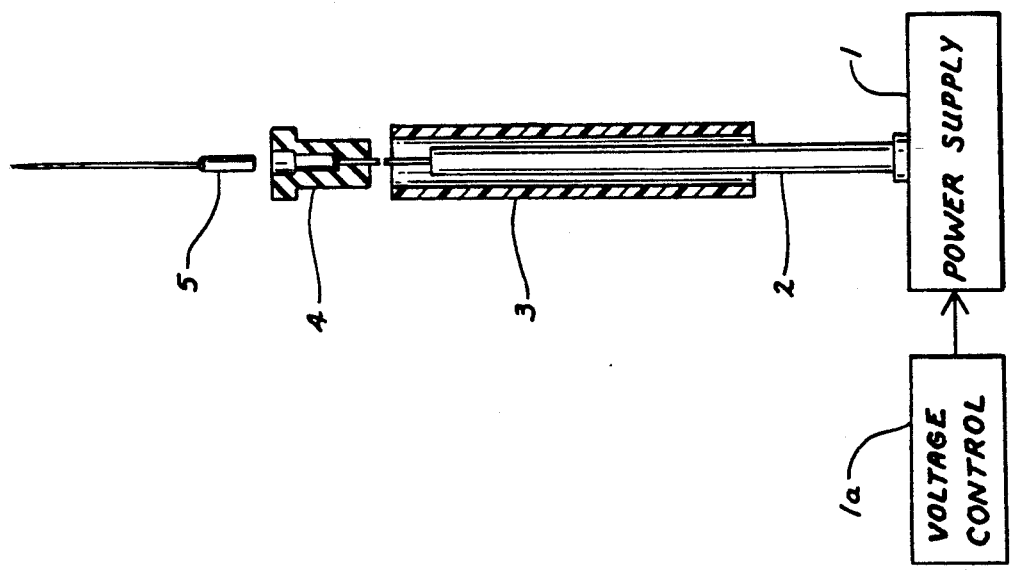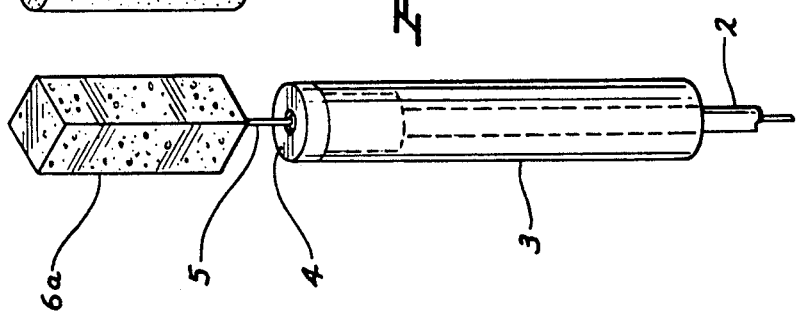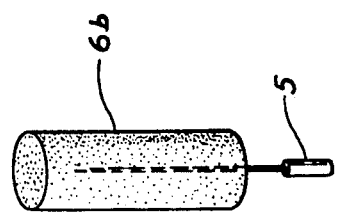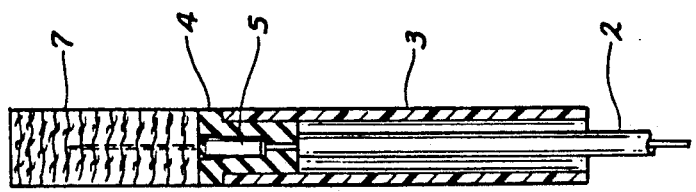

ELECTROSTATIC VAPOR/AEROSOL/AIR ION GENERATOR

BACKGROUND OF THE INVENTION

This invention in general is intended to generate vapor and/or aerosols from a liquid by the application of an electrostatic charge to a porous, semi-conductive, capillament assembly which receives the liquid. More specifically a high voltage DC or AC signal is introduced to a device referred to herein as an "electrostatic wick" or a "vaporizing emitter." This invention has a particular application in the vaporization of essential oils commonly used in the fragrance industry. Essential oils derived from plants, trees, and flowers; also perfumes, natural and synthetic; deodorants, disinfectants, fumigants, fungicides, insecticides, and other liquid substances either water or hydrocarbon based which may be intended to modify, condition, or alter the quality of an indoor or outdoor atmosphere can be vaporized more effectively using such apparatus.

There is a growing concern in the area of indoor air quality often referred to as "sick building syndrome." The modern living and working environment has been designed around energy efficiency and not so oriented around occupant health and comfort. It would be desirable to be able to recreate the properties of fresh outdoor air, indoors. The existence of air ions and their benefit is well documented. Over the last five years there has also been an increased interest in aromatic essences from plants and their application to enhancing or altering the quality of an indoor environment.

The vaporization of aromatic essences and other liquids and also the generation of negative ions is the basis for this invention. The original embodiment of this invention is based upon the need to enhance indoor air quality. This invention can also be modified for applications where it is desirable to generate vapor or aerosols using electrostatic means.

The vaporization of liquids is accomplished by a variety of apparatus and there are also many devices which use electrostatic means to generate aerosols. This invention is specific to the generation of vapor and/or aerosols more efficiently in a range of sizes from a variety of liquids with more control than the prior art, and it can also generate air ions.

The closest prior art was found to be an apparatus for generating a mist of negatively charged liquid aerosols, by Michalchik U.S. Pat. No. 4,776,515. The limitations of the patent based on the claims are that a very specific conductivity of the liquid is required and that charged particles are generated, not a vapor. The device also has specific requirements upon the manner in which the liquid is fed to the capillary in order to maintain the desired aerosol generating effect.

An apparatus for producing a spray of liquid droplets of a specific size range is covered in U.S. Pat. No. 4,829,996. This device is specific to the production of particles by electrostatic means of a certain size and specifically not a vapor. This device is specifically an electrostatic spray generator for an inhaler.

The electrostatic dispersal of liquids by Pollard et al in U.S. Pat. No. 4,400,332 is specific in the use of a porous material having a series of termini which is fed a liquid, namely, petrol fuels. This porous material is charged electrostatically and a spray of fine particles are formed in an air stream. This device produces very fine particles within an air stream wherein an annular enclosure is required. Here again vapor is not mentioned and a moving air stream is required.

Electrostatic enhancement of evaporation by French et al in U.S. Pat. No. 3,771,233 covers a method of specifically improving the evaporation of water from investment cast ceramic molds using an electrostatic charge placed upon the mold. The evaporation process is enhanced with a series of needles of an opposite charge placed near the surface of the mold. This method is specific in claim to the evaporation of water from investment castings. In this case evaporating water is the only objective.

This invention is an improvement upon these methods and others such that both vapor and/or aerosols can be generated from the same device. Another advantage is that the rate of vapor generation can be controlled by the adjustment of the voltage applied to the "emitter," and/or the liquid feed rate and/or the placement of an electrostatic field forming control grid near the emitter. An additional advantage is that various sizes of aerosols can be generated from the same emitter by simple adjustment of these field forming control grids. This invention also will generate air ions of the same polarity as the supply voltage.

SUMMARY OF THE INVENTION

The concept of electrostatic vaporization was conceived in an attempt to disperse a vapor of a conditioning substance and also generate negative air ions into the air of a building to improve indoor air quality. The general embodiment of the invention is comprised of but not limited to the following components.

A high voltage DC power supply with an adjustable output (5-35 kilovolts negative) is used to power an "electrostatic wick" assembly which is comprised of a central conductive electrode, an outer porous capillary material, and a vial, vessel, or tubular enclosure used to contain and direct the liquid to be vaporized. If the liquid is supplied to the apparatus by the use of a tube or pipe and if there is no requirement to "wick" the liquid, then the device is referred to as a "vaporizing emitter." In both devices the main components of the wick or emitter would be summarized as an electrostatically charged, liquid-fed, semi-conductive, porous, capillary assembly.

These "wicks" and "emitters" were fabricated from the following materials in hundreds of combinations in order to obtain the best vapor/aerosol generation performance for the test liquid and also the optimum air ionization output.

Conductive foam, ceramic fibers, graphite fibers, porous ceramic, porous polyethylene foam, porous sintered metals (discs, tubes, spheres, and sheets of stainless steel and brass), glass wool, Fiberglas braiding, graphite braiding, stainless steel braiding, glass tubing, polycarbonate tubing, wool wicking, wool felts, and other materials were used alone and in combination.

In most cases the most efficient "wicks or emitters" for all liquids tested were fabricated from a combination of a conductive center electrode and an outer semi-conductive or nonconductive porous capillary material.

These charged "wicks" or "emitters" directly effect the natural vapor pressure of any liquid which is applied to them at any given temperature and atmospheric pressure by using electrostatic forces acting upon the surface tension of the liquid held within a porous mass or wicking assembly.

The initial objective of this invention was to efficiently vaporize an aromatic essential oil into an office environment. After finding the use of an electrostatic charge applied to a conductive porous mass or wick a highly effective vaporization system, it is necessary to outline additional objectives of the invention.

OBJECTS OF THE INVENTION

The principal object of the present invention is to generate electrostatically charged vapors and aerosols from a liquid using high voltage direct current (DC) which is applied to a vaporizing emitter or wick assembly.

An additional object of this invention is to be able to precisely control the rate of generation of vapor, and/or aerosols by controlling the voltage applied and thereby the electrostatic charge upon the emitter or wick, the electric field pattern and also the volume rate of liquid feed to the wick or emitter.

Another object of this invention is to electrostatically charge the vapors and/or aerosols of the liquid to a desired polarity and through the use of electrostatic fields, control the shape and pattern of the vapor/aerosols that are generated.

An additional object of this invention is to release these charged vapors and aerosols directly into the air of a room, or onto the inner surfaces of ventilation system duct work of a building or onto the surfaces of ventilation system mechanical equipment and/or to distribute the vapor/aerosols throughout a building through the ventilation system.

The final object of this invention is to select specific liquid chemical formulations which in vapor phase and/or aerosol form may be electrostatically charged, will have properties such that when they are introduced into the air of a room or a building ventilation system they will modify the character and quality of the air by adding natural aromas, synthetic scents or combinations which may also include disinfection agents, fungicides, bactericides, viruscides and related formulations which could be used to disinfect building ventilation duct work and related ventilation system equipment.

BRIEF DESCRIPTION OF THE DRAWINGS

The above mentioned introduction to the concept, advantages and the objectives of this invention will be described in more detail and in reference to the following drawings.

FIG. 1*a* shows the most basic embodiment of the concept of the use of electrostatic charges to vaporize a liquid directly from a porous mass or wick. Also shown are the basic components in exploded view.

FIGS. 1*a*–1*d* show different wick embodiments.

FIG. 2 is a perspective view of a preferred embodiment of a "wick" assembly partially in section.

FIG. 3 shows the installation of the "wick" assembly shown in FIG. 2 within a glass bottle. This embodiment is a self-contained liquid storage and vapor/aerosol dispensing device.

FIG. 4 is an illustration of an embodiment of a means to hold the device of FIG. 3 and apply an electrostatic charge to it.

FIG. 5 is an embodiment of a "vaporizing emitter" for use within a moving air stream. This model requires a controlled liquid feed to the emitter in addition to the electrostatic charge.

FIG. 6 is an illustration of another vaporizing emitter which also requires a controlled liquid feed and a moving air stream.

DETAILED DESCRIPTION OF THE PREFERRED EMBODIMENT

In consideration of the drawings submitted and the partial list of materials used to construct these vaporizing emitters, it is not possible to illustrate every combination. These serve as examples that have proven to be effective under test and have demonstrated the concept of the electrostatic vaporization of selected liquids.

FIGS. 1*a*–1*c* illustrate the most basic embodiments of the "electrostatic wick" assembly and its power source. FIG. 1*a* shows an exploded view of the components. A high voltage DC power supply 1 with an adjustable output 1*a* (5–35 kilovolts negative 200 microamps) supplies power to a terminal 4 via a high voltage wire conduit 2. An electrode 5 is inserted in the terminal and provides the charge to the wick assemblies. High voltage terminal 4 is inserted into a polycarbonate tube 3 as a support.

FIG. 1*b* is a view of these components fully assembled to a wick assembly. The electrode is inserted into the wick material or assembly 6*a*, the desired liquid is supplied to the wick and power is applied at the desired voltage. The properties of the materials that comprise the wick have a significant effect upon the vapor and/or aerosol output efficiency at any given voltage setting. The porosity, conductance, and shape of the materials will determine the vapor-aerosol ratio and also the amount of air ions generated.

In FIG. 1*b* the wick material 6*a* is a conductive, carbon-treated foam, which is saturated with the desired liquid and charged by the power supply 1. In this embodiment of the wick, the foam emanates a very strong vapor from all exposed surfaces with the greatest concentration coming from the corners and edges. Wick 6*b* as shown in FIG. 1 *d* is comprised of porous sintered metal. A variety of shapes and metal types were saturated with liquid and placed onto the electrode. As with the carbon foam they also generated vapor with the greatest concentration coming from the corners and edges. This follows the general rule that corona discharge will form at points or sharp radius edges. The liquid that is near these areas is carried away by this discharge forming an electrified vapor.

FIG. 1*c* shows an embodiment of the same electrode support as in FIG. 1*b* with a wick 7 that is fabricated from a nonconductive porous material such as wool felt, porous polypropylene or similar material. The wick material is saturated with the desired aromatic liquid. The electrode is preferably inserted into the wick so that the entire electrode is covered by the wick. In this embodiment, the wick must conduct the full charge that is supplied to the electrode. The liquid provides a means of conducting the charge from the center of the wick to the outer surfaces where vaporization takes place in the same manner as the wicks that are conductive. This embodiment requires a higher voltage to generate the same amount of vapors as the wicks described in FIG. a*b*.

FIG. 2 details a modified design of a wick or emitter assembly 16 in comparison to the wicks shown in FIG. 1. Wick assembly 16 is comprised of a center electrode assembly which is made of ceramic fibers 8 in which are embedded stainless steel wires 9. Fibers 8 are preferably formed into a plurality of elongated capillament bundles 8a as shown. The fibers 8 may be braided or twisted with wires 8 either extending straight therein or intertwined with the fibers. This core is covered by a glass fiber braid in the form of a sleeve 10 preferably comprised of a plurality of separate capillament bundles of fine fibers or filaments which are exposed at 10b at the top of the assembly. An outer cover of glass tubing 11 may also be provided if the sleeve 10 does not provide a sufficiently strong, liquid impervious outer layer. In this design the inner conductive fiber core contacts the electrode 5, which preferably extends at least partially into the inner core of capillaments 8a as shown. It also holds the liquid that is transferred to the glass fiber braid. The core wires 9 help shape the electric field which in turn effects the vapor-aerosol pattern and also the air ion output. The outer glass fiber braid 10 moves the liquid by capillary action from bottom fibers 10a to the top through exposed top fibers 10b where the electrostatic field breaks down the surface tension of the liquid, and from the very tips 10c of the glass fibers the liquid is converted to vapor and/or aerosols and released. Capillament bundles 8a also assist in moving the liquid through the assembly 16 by wicking or capillary action.

This design also is a very effective air ion emitter. This illustration is an example of the concept of using a number of materials which together have the desired properties of porosity, conductance, and capillary action, and will generate vapor and/or aerosols when electrified by a voltage high enough to break the surface tension of the desired liquid.

Figure 3:
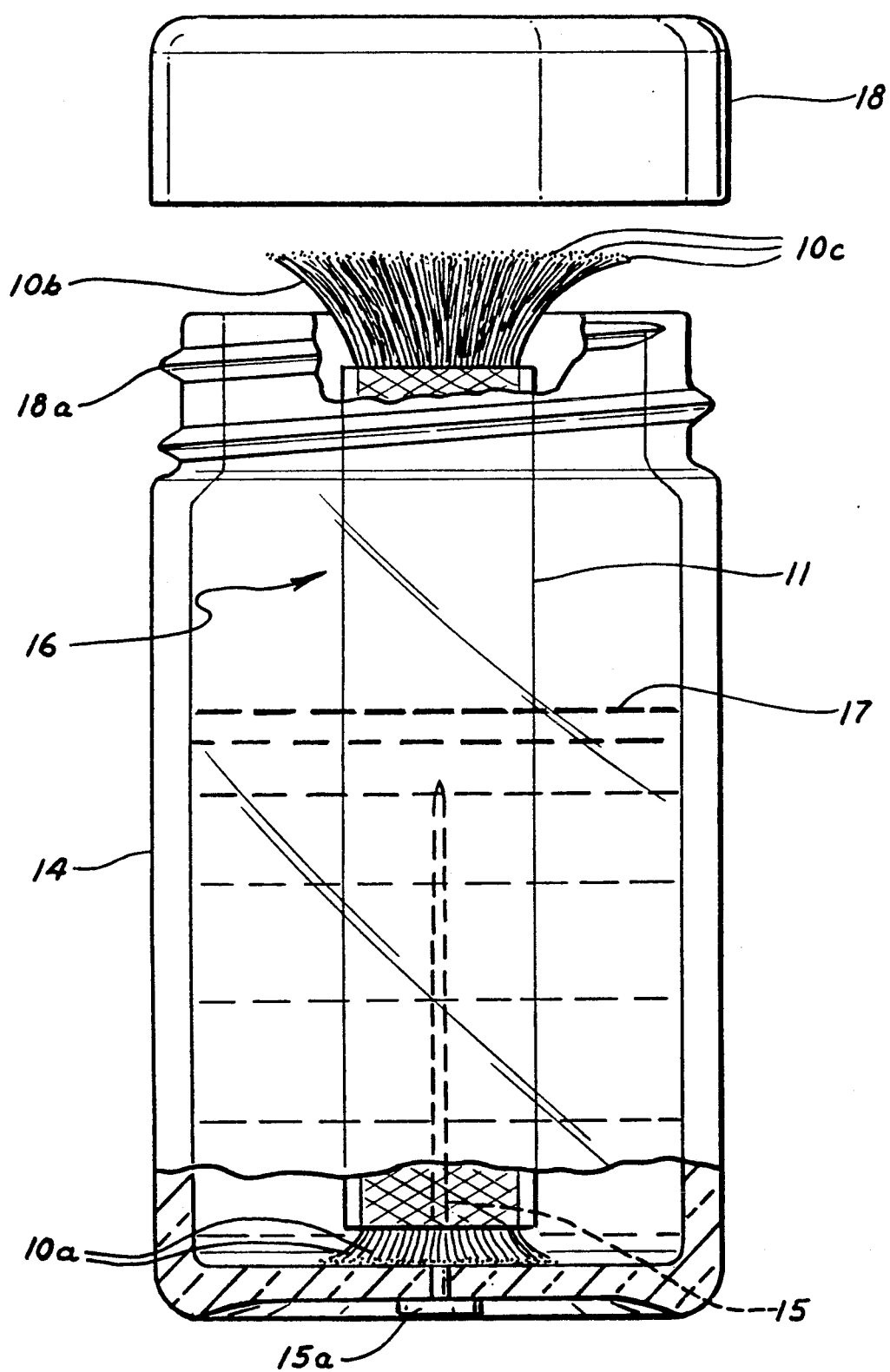

FIG. 3 is a preferred embodiment of a device that will also provide a means of containing the liquid that would be supplied to the wick assembly 16 of FIG. 2. In this embodiment a glass bottle 14 contains the wick assembly 16 and has a high voltage electrode 15 which extends through the bottom of the bottle. It also has a contact terminal 15a on the bottom of the bottle in order to provide a means of supplying a charge to the wick assembly 16. The desired liquid 17 is contained within the bottle and is continuously moved to the top of the wick by capillary action. That action is enhanced by the extension of fiber end segments 10a into the liquid at the lower end of wick assembly 16. The bottle can be sealed by a cap 18 and stored for later use without loss of liquid due to evaporation or spilling. This embodiment is a self-contained system that will generate vapor and/or aerosols and also air ions when it is provided a high voltage DC signal to the base electrode and the bottle cap 18 is removed. A threaded cap 18 may be used for attachment to threads 18a on bottle 14.

Figure 4:
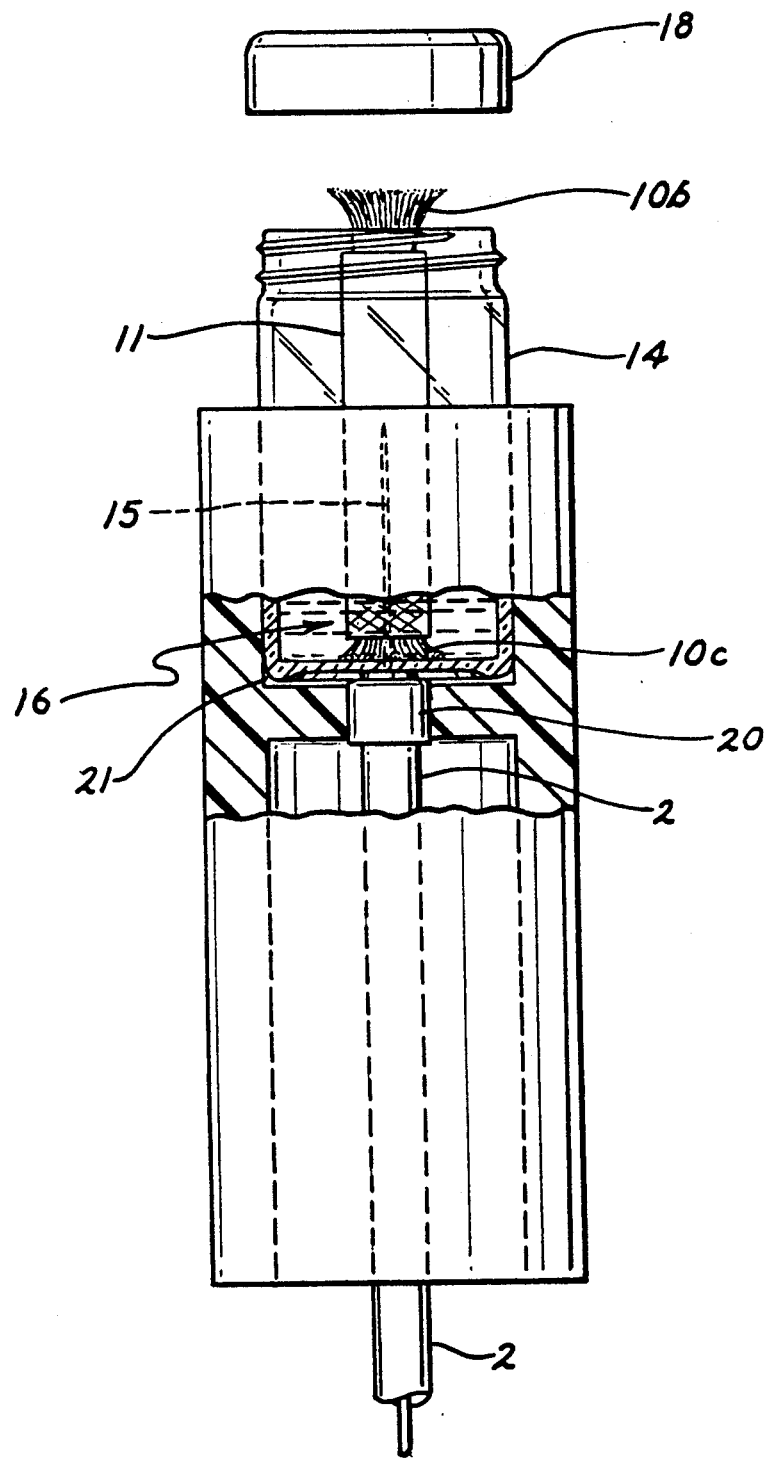
Figure 9:
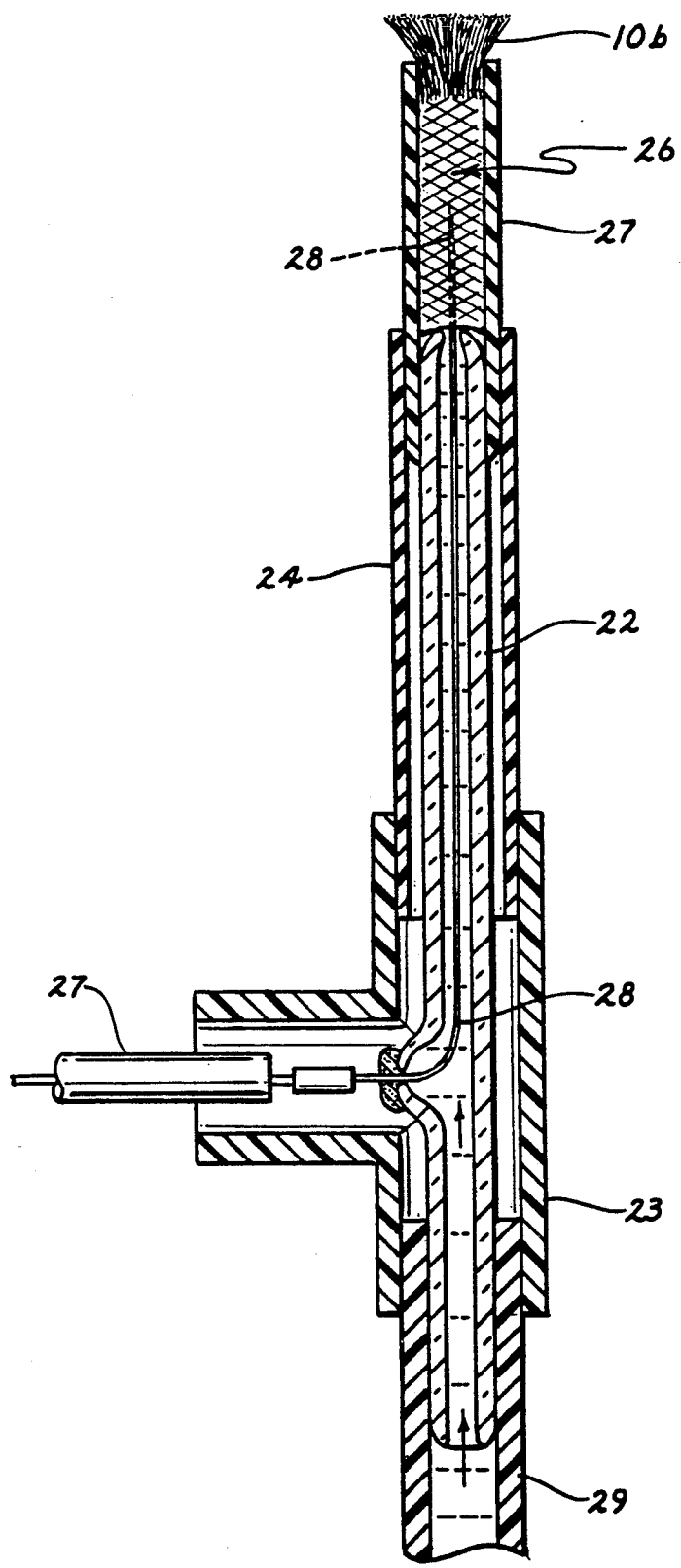

FIG. 4 shows an embodiment of a device that holds the vaporizing bottles detailed in FIG. 3. The device is comprised of an insulating support 19 made of porcelain, glass, plastic, or similar material. A high voltage DC signal is supplied to the contact terminal connector 20 by a high voltage wire 2. The electrode contact 15a of the bottle 14 makes contact with the power contact 20 as shown. This provides power to the wick assembly 16 and causes the vapor and/or aerosols to emanate from the top of the bottle into the air. The bottle 14 is secured within the recess 21 of the support column.

FIG. 5 is an illustration of an embodiment of a "vaporizing emitter." The emitter is comprised of the following: a glass capillary tube 22 fitted securely within a modified fluid TEE connector 23, and a polycarbonate tube 24 which serves to protect the glass capillary tube and also couples the electrostatic wick assembly 26 to the tip 25 of the capillary tube 22. In this embodiment, the glass tube 11 from FIG. 2 is replaced with a larger tapered fluoroplastic tube 27 which supports and protects the "wick" assembly 26. Otherwise, the wick assembly may be the same as that shown at 16 in FIG. 2. The high voltage is supplied through wire conduit 2 to a Nichrome wire 28 which is inserted into the capillary tube 22 and makes contact with the center core of the wick assembly 26 at the tip of the glass capillary tube. In this design liquid is supplied to the glass capillary 22 through a tube 29 from a fluid control system which meters the desired amount of liquid to the vaporizing emitter assembly. A suitable liquid pump connected to a supply source of desired liquid may be used to provide the metered flow of liquid. The liquid may be an aromatic essence, deodorant, disinfectant, fumigant, fungicide, insecticide, or bactericide.

A moving air stream may be used to remove the generated vapor. In this design the vapor control is achieved by controlling the liquid feed rate, the high voltage, and the air stream velocity.

Figure 6:
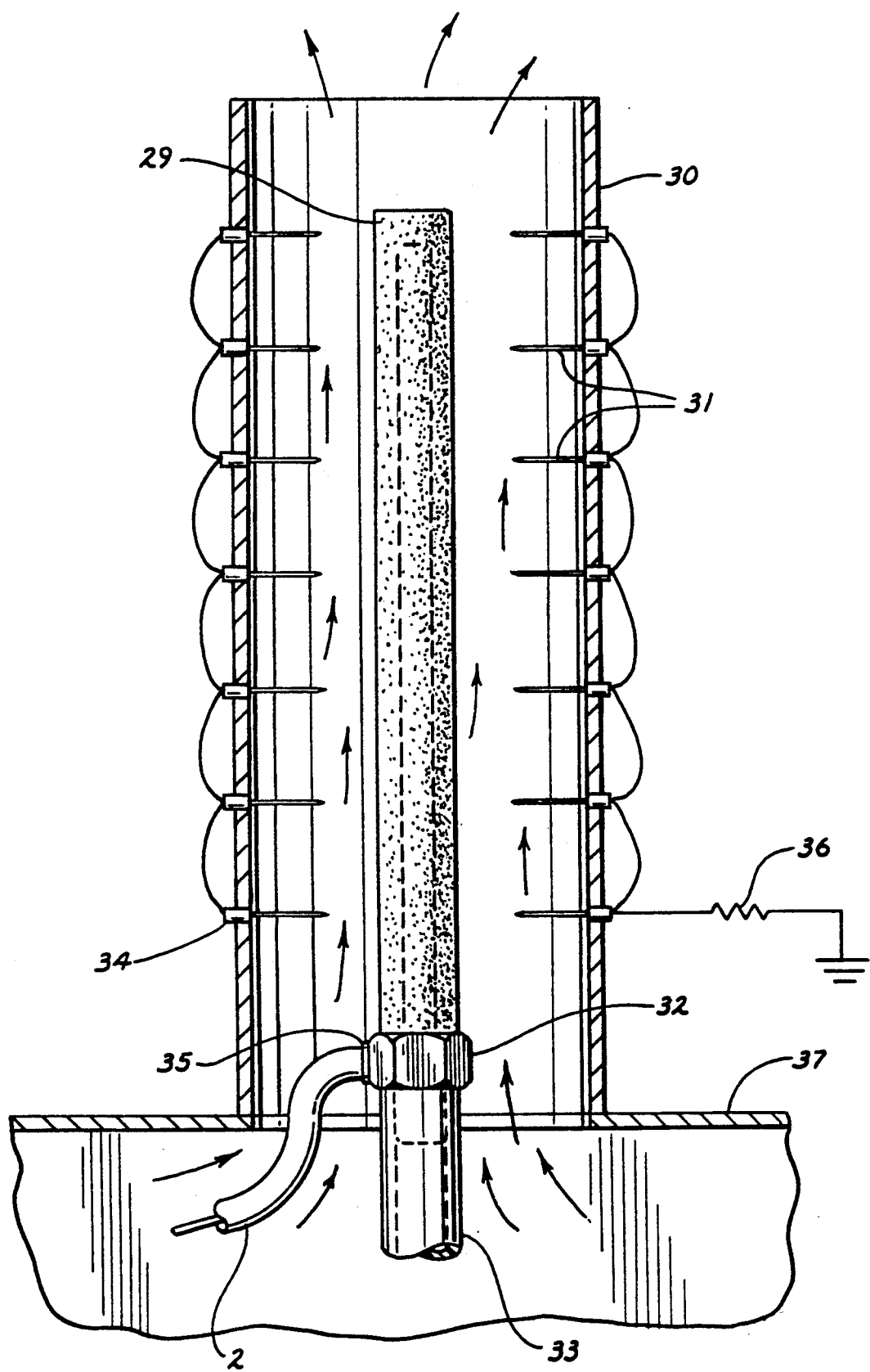

FIG. 6 is an illustration of another embodiment of a vaporizing emitter based upon the use of a porous metal tube 29 which is surrounded by a control grid cylindrical enclosure tube 30 which contains a plurality of needles 31 positioned around the circumference and also along the length of the porous metal emitter tube 29. These needles or points are connected together electrically and may be powered by a DC or AC signal provided at 34 or connected to ground through a resistor 36 or directly. The porous metal tube 29 is configured to be supplied with the desired fluid by means of a fluid connection 32 and a fluid feed line 33. The fluid feed rate is controlled by automatic or manual means. The high voltage DC signal 2 is supplied to the porous tube by a contact ring 35 on connector fitting 32 in order to provide the electrostatic charge to the porous metal tube. The position of the plurality of needles near this tube causes the formation of a high concentration of electric field lines, and as a result there is a breakdown of the vapor pressure of the liquid which has saturated the metal tube. The area under each needle becomes an "active region" of vapor and/or aerosol generation. The generated vapor and/or aerosols are removed from the confinement of the enclosure tube by some means of air flow through the tube.

By controlling the voltage and the liquid feed rate supplied to the porous emitter tube, and the signal or ground applied to the needle array, and the air flow rate through the enclosure tube 30, it is possible to control the aerosol and/or vapor generation output of the device.

It is to be understood that the wick assembly 16 of FIG. 2 may readily be substituted for the porous metal tube 29 as the vapor or aerosol emitter inside of air passage, enclosure tube 30. In such an embodiment, the secondary electrodes in the form of needles 31 would not be required and would not be used. As with the embodiment of FIG. 5 described above, a desired liquid would be supplied in metered amounts, as from a pump, to supply line 33, and thence into the wick assembly 16, and a moving air stream would be used to remove the generated vapor. For that purpose, a blower (not shown) is provided in housing 37 to provide a pressurized stream of air through tube 30 and over the vapor emitter assembly. Any of the liquids described above may be supplied through supply line 33, and the generated vapors may be released directly into a room.

In summary, the embodiments of these devices which have been described above serve to illustrate a novel method of being able to generate liquid based aerosols, vapors and also air ions with a variety of means of control over the quantity of vapor and/or aerosols, the size of the aerosols and also air ions. The fundamental base of these methods, devices, and apparatus is based upon the use of electrostatic charges being applied to a semi-conductive, wick-like, porous, capillament assembly which is also supplied with the desired liquid which is to be vaporized. In addition, the placement of a control grid assembly within or near the aerosol/vapor generation zone will provide a means of effecting the electric field concentration and pattern thereby also having an influence upon the aerosol/vapor/air ion generation.

The foregoing description of the preferred embodiments of this invention has been presented for the purposes of illustration and description. It is not intended to be exhaustive or to limit the invention to the precise form disclosed. Many modifications and variations are possible in the light of the above teaching. It is intended that the scope of the invention be limited not by this detailed description, but rather by the claims appended hereto.

What is claimed is:

1. Apparatus for generating electrostatically charged aerosols and vapors comprising:
   a porous, capillary unit of elongated configuration having a vapor dispensing end;
   electrode means, said electrode means consisting essentially of a single electrode disposed in close proximity to said capillary unit;
   electrical contact means on said electrode for connecting said electrode to a source of high voltage, direct current (DC) power; and
   means for supplying liquid to said capillary unit, whereby liquid passes through said porous capillary unit in proximity to said electrode and is electrostatically charged and dispensed as vapor or aerosol from said dispensing end of said capillary unit.

2. Apparatus as defined in claim 1 wherein:
   said porous, capillary unit is comprised of a plurality of fiber filaments arranged in a tubular configuration which terminate at said dispensing end in a plurality of exposed, vapor-dispensing tips.

3. Apparatus as defined in claim 1 wherein:
   said fiber filaments are braided into capillament bundles, the extremities of which at said dispensing end of said capillary unit are open and unbraided to provide freely extending, filament tip extremities defining said dispensing tips.

4. Apparatus as defined in claim 1 wherein:
   said capillary unit further comprises a central, elongated core made up of a plurality of semi-conductive capilaments through which liquid may pass, with said central core being positioned inside of said tubular configuration of fiber filaments in electrically conductive relation with said electrode.

5. Apparatus as defined in claim 4 wherein:
   said capillaments each comprise a bundle of fibers in which a wire conductor is embedded.

6. Apparatus as defined in claim 5 wherein:
   said electrode is elongated and extends at least partially into said core substantially centrally thereof.

7. Apparatus as defined in claim 1 wherein:
   said capillary unit is contained within an outer, liquid impervious vessel which holds a supply of liquid and comprises said means for supplying liquid to said capillary unit.

8. Apparatus as defined in claim 7 wherein:
   said fiber filaments terminate at their lower ends in end segments which extend into the liquid within the vessel.

9. Apparatus as defined in claim 7 and further including an electrically insulating holder having an upwardly opening recess within which said vessel is removably received for vapor dispensing operation, said holder having electrical connector means therein for connecting said electrical contact means on said electrode to a power supply wire.

10. Apparatus as defined in claim 4 wherein:
    said capillary unit is contained and protected in an outer, liquid impervious tubular member.

11. Apparatus as defined in claim 1, and further including:
    a tubular passage within which said capillary unit is positioned;
    said means for supplying liquid comprises a liquid supply line connected to said capillary unit; and
    means for delivering a pressurized stream of air into said tubular passage for flow over said capillary unit and removal of vapors emitted from said capillary unit.

12. Apparatus as defined in claim 11 wherein:
    said capillary unit is comprises of a plurality of fiber filaments arranged in a tubular configuration, and a central, elongated core made up of a plurality of semi-conductive capillaments through which liquid may pass, with said core being positioned inside of said tubular configuration of fiber filaments in electrically conductive relation with said electrode.

13. Apparatus as defined in claim 12 wherein:
    capillaments each comprise a bundle of fibers in which a wire conductor is embedded.

14. Apparatus for generating electrostatically charged vapors and aerosols for release into a room comprising:
    a porous, capillary unit of elongated configuration having a vapor dispensing end terminating in a plurality of filaments;
    electrode means, said electrode means consisting essentially of a single electrode disposed in close proximity to said capillary unit;
    electrical contact means on said electrode for connecting said electrode to a source of high voltage, direct current (DC) power;
    means for supplying liquid to said capillary unit, whereby liquid passes through said capillary unit in proximity to said electrode and is electrostatically charged and dispensed as a vapor or aerosol from said dispensing end of said capillary unit, said liquid supplying means comprising an outer, liquid impervious vessel which holds a supply of liquid; and
    an electrically insulating holder having an upwardly opening recess within which said vessel is removably received for vapor dispensing operation.

15. Apparatus as defined in claim 14 wherein:
    said capillary unit is comprised of a plurality of fiber filaments arranged in a tubular configuration.

16. Apparatus as defined in claim 15 wherein:
    said capillary unit further comprises a central, elongated core made up of a plurality of semi-conductive capillaments through which liquid may pass, said central core being positioned inside of said tubular configuration of fiber filaments in electrically conductive relation with said electrode.

* * * * *

UNITED STATES PATENT AND TRADEMARK OFFICE
CERTIFICATE OF CORRECTION

PATENT NO. : 5,196,171
DATED : March 23, 1993
INVENTOR(S) : Mark E. Peltier

It is certified that error appears in the above-indentified patent and that said Letters Patent is hereby corrected as shown below:

Column 3, line 54, delete "1a" and substitute --1b--.

Claim 3, Column 7, line 47, delete "1" and substitute --2--.
Claim 4, Column 7, line 53, delete "1" and substitute --2--.
Claim 7, Column 7, line 66, delete "1" and substitute --2--.
Claim 11, Column 8, line 16, delete "1" and substitute --2--.
Claim 12, Column 8, line 27, delete "comprises" and substitute --comprised--.
Claim 13, Column 8, line 36, insert the word --said-- before the word "capillaments".

Signed and Sealed this

Tenth Day of May, 1994

BRUCE LEHMAN

*Attest:*

*Attesting Officer*    Commissioner of Patents and Trademarks